United States Patent

Miyashita et al.

[11] Patent Number: 5,449,787
[45] Date of Patent: Sep. 12, 1995

[54] N,N'-DISUBSTITUTED AMIDE DERIVATIVES

[75] Inventors: Mitsutomo Miyashita, Okaya; Toshio Maeda, Suwa; Fumio Kawahara, Nogi; Fukutaro Taga, Saitama, all of Japan

[73] Assignee: Kyorin Pharmaceutical Co., Ltd., Tokyo, Japan

[21] Appl. No.: 290,785

[22] PCT Filed: Mar. 3, 1993

[86] PCT No.: PCT/JP93/00269

§ 371 Date: Sep. 6, 1994

§ 102(e) Date: Sep. 6, 1994

[87] PCT Pub. No.: WO93/18025

PCT Pub. Date: Sep. 16, 1993

[30] Foreign Application Priority Data

Mar. 9, 1992 [JP] Japan .................. 4-084994

[51] Int. Cl.⁶ .................. A61K 31/415; A61K 31/40; C07D 231/56; C07D 209/12
[52] U.S. Cl. .................. 548/362.5; 548/468
[58] Field of Search .................. 514/406, 414, 403; 548/362.5, 468

[56] References Cited

U.S. PATENT DOCUMENTS 4,558,048  12/1985  Bass .................. 514/232
4,959,375   9/1990  Ward .................. 514/323

Primary Examiner—Peter O'Sullivan
Attorney, Agent, or Firm—Oblon, Spivak, McClelland, Maier & Neustadt

[57] ABSTRACT

N,N'-disubstituted amide derivatives having potent and selective antagonistic action to 5-HT₃ receptor have been developed by the present invention, which provides antagonistic drugs to 5-HT₃ receptor containing novel N,N'-disubstituted amide derivatives represented by a general formula [I]

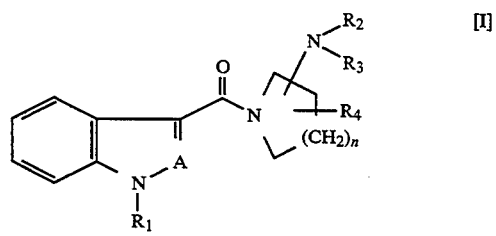

(wherein $R_1$ denotes a hydrogen atom or lower alkyl group, $R_2$ and $R_3$, which may be identical or different, denote respectively a hydrogen atom, lower alkyl group, lower alkenyl group, nonsubstituted or substituted aryl-lower alkyl group, acyl group or lower alkoxycarbonyl group, $R_4$ denotes a hydrogen atom, lower alkyl group or lower alkoxy group, A denotes CH or N, and n denotes 1), their hydrates or acid addition salts.

6 Claims, No Drawings

N,N'-DISUBSTITUTED AMIDE DERIVATIVES

SPECIFICATION

This application is a 371 of PCT/JP93/00269 filed Mar. 3, 1993.

TECHNICAL FIELD

The present invention relates to novel N,N'-disubstituted amide derivatives. In more detail, it is concerned with novel N,N'-disubstituted amide derivatives and their pharmaceutically admissible acid addition salts, which show an antagonisic action to 5-HT$_3$ receptor and which are useful as antiemetics, alimentary tract motor function modulators, antimigraine agents, antipsychotics, anxiolytics, etc., and preparative processes therefor.

BACKGROUND TECHNOLOGIES

So far, as antagonists to 5-HT$_3$ receptors, those having an azabicyclo ring moiety described in Japanese Unexamined Patent Publication Nos. Sho 58-978, Sho 59-36675, Sho 61-275276, Hei 1-104072 and Hei 1-106882, those having an imidazole ring moiety described in Japanese Unexamined Patent Publication Nos. Sho 60-214784, Sho 63-211279, Hei 2-131485 and Hei 3-2180, and the like are known.

As result of our diligent study for purpose of finding out such compounds having potent and selective antagonistic action to the 5-HT$_3$ receptor, the inventors of the present invention have found N,N'-disubstituted amide derivatives which satisfy said purpose and have a different chemical structure from that of known compounds, leading to completion of the invention.

DISCLOSURE OF THE INVENTION

The present invention relates to novel compounds represented by a general formula [I]

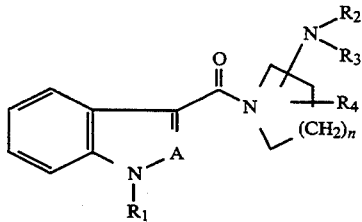

(wherein R$_1$ denotes a hydrogen atom or lower alkyl group, R$_2$ and R$_3$, which may be identical or different, denote respectively a hydrogen atom, lower alkyl group, lower alkenyl group, nonsubstituted or substituted aryl-lower alkyl group, acyl group or lower alkoxycarbonyl group, R$_4$ denotes a hydrogen atom, lower alkyl group or lower alkoxy group, A denotes CH or N, and n denote 1, 2 or 3).

The addition salts of the compounds represented by the general formula [I] are preferably physiologically admissible salts. For example, their salts with an inorganic acid such as hydrochloric acid, hydrobromic acid, sulfuric acid, phosphoric acid, etc. and their salts with an organic acid such as acetic acid, propionic acid, citric acid, lactic acid, maleic acid, fumaric acid, succinic acid, tartaric acid, methanesulfonic acid, etc. can be mentioned.

The compounds of general formula [I] include stereoisomers, optical isomers and mixtures thereof. Moreover, the compounds [I] often exist as their hydrates and solyates, so these hydrates and solyates are also included in the compounds of the present invention.

The terms in this specification will be explained hereinafter.

For "lower alkyl group", a straight- or branched-chains with carbon atoms of 1 to 6 such as methyl group, ethyl, n-propyl, i-propyl, etc. is mentioned.

For "lower alkenyl group" a straight- or branched-chains with carbon atoms of 2 to 6 having a double bond at one or more locations such as vinyl, allyl, etc. is mentioned.

"Nonsubstituted or substituted aryl-lower alkyl group" means one having non-substituted aryl portion or one having aryl portion substituted with 1 to 5 halogen atoms (fluorine, chlorine, bromine or iodine), lower alkyl group, trifluoromethyl group, hydroxyl group, lower alkoxy group, cyano group, amino group, monosubstituted amino group, disubstituted amino group, acylamino group, nitro group, carboxyl group or lower alkoxycarbonyl group.

"Acyl group" means non-substituted or substituted saturated aliphatic carboxylic acid residue such as formyl, acetyl, propionyl and so on.

For "lower alkoxycarbonyl group", one in which its lower alkyl portion is a straight- or branched-chain having carbon atoms of 1 to 6 such as methoxycarbonyl, ethoxycarbonyl, propoxycarbonyl, etc. is mentioned.

For "lower alkoxy group", one in which its lower alkyl portion is methyl, ethyl, propyl, butyl, etc. is mentioned.

The compounds of the present invention represented by the general formula [I] can be prepared through following processes.

(Preparative process 1)

They can be prepared by reacting a carboxylic acid represented by a general formula [II]

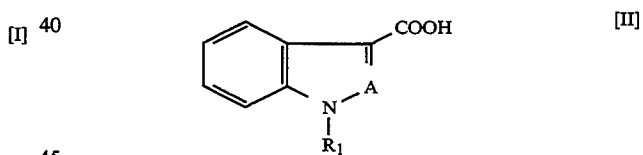

(wherein each symbol has the same meaning as above), or its reactive derivative with a compound represented by a general formula [III],

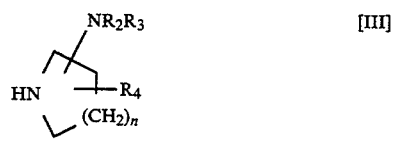

(wherein each symbol has the same meaning as above).

As the reactive derivative of the compounds of represented by the general formula [II], for example, a lower alkyl ester, active ester, acid anhydride, acid halide, dimer when R$_1$ is a hydrogen atom in [II] [e.g. refer to J. Org. Chem., 23, 621 (1958)], etc. can be mentioned. As the concrete examples for active ester, p-nitrophenyl ester, pentachlorophenyl ester, N-hydroxysuccinimido ester, etc. are mentioned. As tile acid anhydrides, a symmetric type acid anhydride or a mixed acid anhydride is used, and, as the concrete example for the mixed acid anhydride, a mixed acid anhydride with alkyl chlorocarbonate ester such as methyl chlorocarbonate, ethyl chlorocarbonate, or the like is mentioned.

Depending on a type of reactive derivative of the compound of the general formula [II], it is sometimes preferable to react in the presence of a base. As the base at that time, an inorganic base such as sodium hydrogencarbonate, potassium hydrogencarbonate, sodium carbonate and potassium. carbonate, and an organic base such as triethylamine, diisopropylethylamine, dimethylaniline, pyridine or the like are used.

When using a compound of the general formula [II], the reaction can be conducted in the presence of a condensing agent such as dicyclohexylcarbodiimide, 1-ethyl-3-(3-dimethylaminopropyl)carbodiimide hydrochloride, N,N'-carbonydiimidazole, or the like.

The reaction of a compound of tile general formula [II]or its reactive derivative with a compound of the general formula [III]is conducted in a solvent or without using the solvent. The solvent to be used is not particularly restricted, if it does not participate in the reaction. For example, benzene, toluene, diethyl ether, tetrahydrofuran, dioxane, methylene chloride, chloroform, ethyl acetate, acetonitrile, N,N-dimethylformamide, etc. are mentioned, and these solvents are used solely or in mixtures of two or more. The reaction temperature differs depending on types, etc. of the raw material compound to be used, but it ranges usually from $-30°$ C. to $200°$ C., preferably from $-10°$ C. to $150°$ C.

(Preparative process 2 )

When $R_2$ and $R_3$ are identical or either of $R_2$ and $R_3$ is hydrogen atom in the general formula [I], the compound of the present invention can be prepared through a following reaction route.

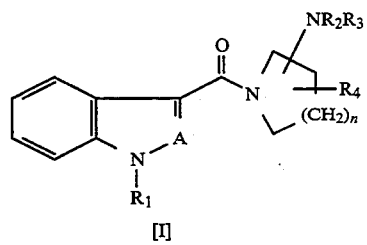

[I]

(in the above route, $R_5$ denotes a protecting group such as benzyloxycarbonyl, t-butoxycarbonyl, benzyl or the like, and the other symbols have the same meaning as the above).

Namely, by reacting a carboxylic acid represented by the general formula [II]or its reactive derivative with the compound [IV]according to the preparative process 1, the compounds [V]can be obtained. By deprotecting the compound [V]according to a usual method, the compound [VI]can be obtained. By applying various methods which are hitherto publicly known to the compound [VI], $R_2$ and $R_3$ can be introduced to give the compound [I].

(Preparative process 3)

When either of $R_2$ and $R_3$ is a hydrogen atom, or $R_2$ and $R_3$ are different and neither of them is a hydrogen atom in the general formula [I], the compound of the present invention can be prepared through a following reaction route.

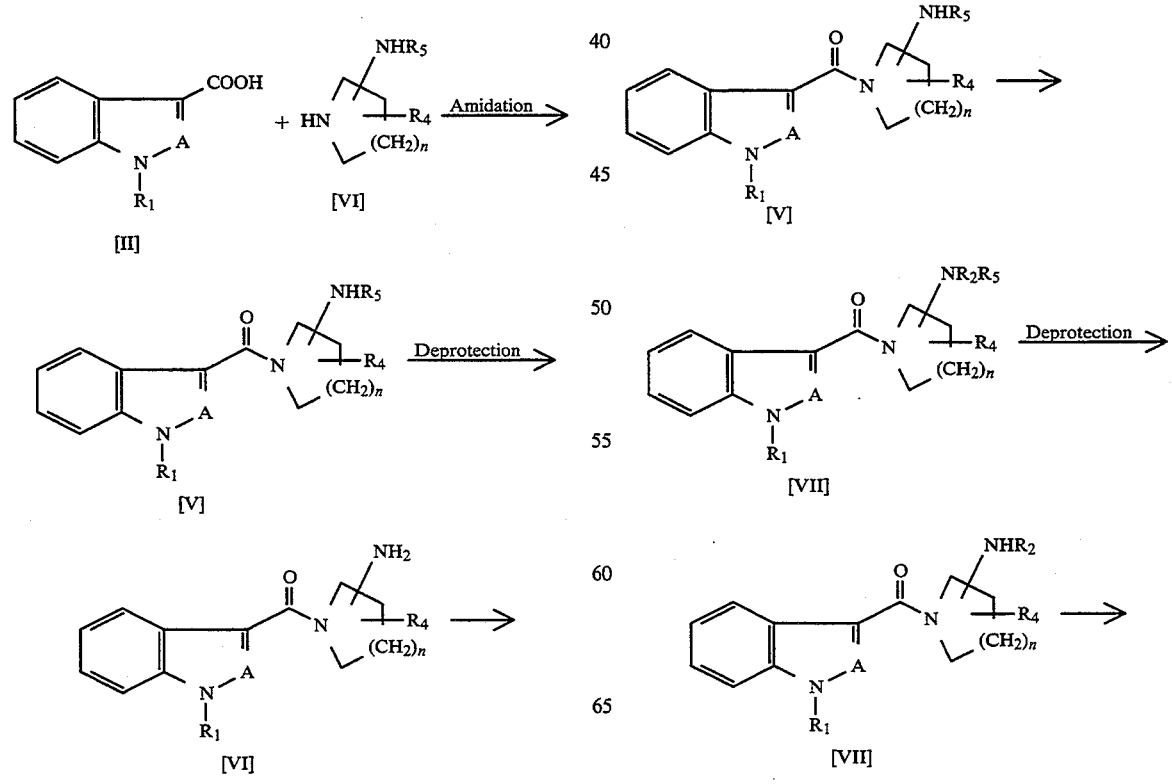

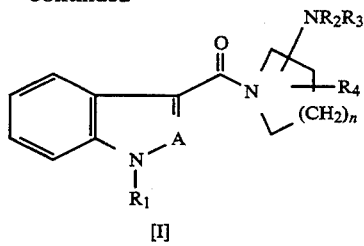

(in the above route, each symbol has the same meaning as the above).

By applying various methods which are hitherto publicly known to the compound [V], $R_2$ can be introduced to give the compound [VII]. By deprotecting the compound [VII] according to a usual method, compound [VIII] is obtained. By applying various methods which are hitherto publicly known to the compound [VIII], $R_3$ can be introduced to give the compound The compound of the present invention has an antagonistic action to 5-HT receptor, in particular, to 5-HT$_3$ receptor. Affinity of the compound of the present invention to 5-HT$_3$receptor is shown by a receptor-binding assay [refer to Gavin J. Kilpatrick et al, Eur. J. Pharmacol., 159, 157 (1989)] using [$^3$H]GR65630 for a tracer legend. Moreover, the antagonistic action to 5-HT$_3$ receptor is shown through inhibition of yon Bezold Jarisch reflex caused by intravenously administering 5-HT to rat.

The compound of the present invention is useful for prevention and/or therapy of diseases described below; nausea and vomitting, in particular, nausea and vomitting caused through administration of anti-cancer drug or radiotherapy; disorders of central nervous system such as migraine, dysmnesia, dementia, depressive symptoms, anxiety and psychosis; dependence resulting from drug abuse; or alimentary diseases such as alimentary indefinite complaint, diarrhea, disorders of alimentary tract motor function and the like.

Best embodiment to put the present invention into practice

In following, the invention will be illustrated concretely based on examples, but the present invention is not confined to these.

Example 1

Cis-3-amino-4-methyl-1-(1-methylindazol-3-ylcarbonyl)-pyrrolidine hydrochloride (1) To a solution of 2.00 g (11.35 mmol) of 1-methylindazole-3-carboxylic acid in 30 ml of DMF was added 1.84 g (11.35 mmol) of CDI at room temperature, and the mixture was stirred for 2 hours at the same temperature. To this solution was added a solution of 2.50 g (12.48 mmol) of cis-3-t-butoxycarbonylamino-4-methylpyrrolidine in 10 ml of DMF at room temperature, the mixture was stirred overnight at room temperature. After completion of the reaction, DMF was distilled off and concentrated residue was purified with silica gel column chromatography (methylene chloride:methanol =30:1). By crystalizing from ether, 2.26 g (76.1%) of cis-3-t-butoxycarbonylamino-4-methyl-1-(1-methylindazol-3-ylcarbonyl)pyrrolidine was obtained. m.p. 186°–187 ° C.

(2) To a suspension of 2.20 g (6.14 mmol) of cis-3-t-butoxycarbonylamino-4-methyl-1-(1-methylindazol-3-ylcarbonyl)pyrrolidine in 22 ml of ethanol was added 11 ml of ethanol saturated with hydrogen chloride at room temperature, and then the mixture was stirred for 3 hours at room temperature. After completion of the reaction, solvent was distilled off and resultant residue was crystallized with addition of dioxane to give 1.81 g (quantitative) of aimed compound. m.p. 177°–180 ° C.

Example 2

Cis-3-diethylamino-4-methyl-1-(1-methylindazol-3-ylcarbonyl)pyrrolidine

Into 2 ml of DMF were dissolved 200 mg (0.68 mmol) of cis-3-amino-4-methyl-1-(1-methylindazol-3-ylcaronyl)pyrrolidine hydrochloride and 0.11 ml (0.81 mmol) of triethylamine, and 0.11 ml (1.36 mmol) of ethyl iodide was added dropwise under ice cooling. After stirring overnight at room temperature, insolubles were filtered off. After addition of 40 ml of water, the solution was made alkaline with sodium bicarbonate, which was then extracted with methylene chloride. After dried over anhydrous magnesium sulfate, the solution was concentrated under reduced pressure to obtain crude oil. This was subjected to silica gel column chromatographic purification (methylene chloride:methanol=10:1) to obtain 100 mg (46.9%) of aimed compound (pale yellow oil).

Example 3

Cis -3 -dimethylamino-4 -methyl-1- (1-methylindazol-3-ylcarbonyl)pyrrolidine hydrochloride Into 18 ml of DMF were dissolved 1.79 g (6.07 mmol) of cis-3-amino-4-methyl-1-(1-methylindazol-3-ylcarbonyl)pyrrolidine hydrochloride and 1.88 ml (13.35 mmol) of triethylamine, and 0.95 ml (15.26 mmol) of methyl iodide was added dropwise under ice cooling. Then, mixture was stirred for 0.5 hours at the same temperature, for 2 hours at room temperature and further for 2 hours at 35°–40 ° C. DMF was distilled off under reduced pressure and to the residue was added water. Then, the solution was made alkaline with 5N aqueous solution of sodium hydroxide, which was then extracted with methylene chloride. After washed with saturated saline solution and dried over anhydrous magnesium sulfate, the solution was concentrated under reduced pressure to obtain orange oil. This was subjected to silica gel column chromatographic purification (methylene chloride: methanol=30:1) to obtain 0.79 g (45.4%) of pale orange oil. To solution of 0.79 g of this oil in 3 ml of ethanol was added 1 ml of ethanol saturated with hydrogen chloride under cooling with ice. Solvent was distilled off and resultant residue was crystallized with addition of dioxane to give 0.75 g (38.3%) of aimed compound. m.p. 224°–227 ° C.

Example 4

Cis-3-n-propylamino-4-methyl-1-(1-methylindazol-3-ylcarbonyl)pyrrolidine

Into 2 ml of DMF were dissolved 200 mg (0.68 mmol) of cis-3-amino-4-methyl-1-(1-methylindazol-3-ylcarbonyl)pyrrolidine hydrochloride and 0.11 ml (0.81 mmol) of triethylamine, and 188 mg (1.36 mmol) of n-propyl methanesulfonate was added under ice cooling. Then, the mixture was stirred for 5 hours at room temperature, for 3 hours at 60 ° C. and further for 5 hours at 70 ° C. After addition of water, the solution was made alkaline with sodium bicarbonate, which was then extracted with methylene chloride. After washed with saturated saline solution and dried over anhydrous magnesium sulfate, the solution was concentrated under reduced pressure to obtain crude oil. This was subjected to silica gel column chromatographic purification (methylene chloride:methanol=20:1) to obtain 57 mg (27.9%) of aimed compound (pale yellow oil).

Example 5

Cis-3-acetylamino-4-methyl-1-(1-methylindazol-3-ylcarbonyl)pyrrolidine

To 200 mg (0.68 mmol) of cis-3-amino-4-methyl-1-(1-methylindazol-3-ylcarbonyl)pyrrolidine hydrochloride was added 0.7 ml of pyridine, and 0.07 ml (0.75 mmol) of acetic anhydride was added dropwise under ice cooling. Then, after heated to room temperature, the mixture was stirred overnight. To the reaction mixture was added water, and then the solution was extracted with methylene chloride. After washed with saturated saline solution and dried over anhydrous magnesium sulfate, the solution was concentrated under reduced pressure to obtain crude oil. This was subjected to silica gel column chromatographic purification (methylene chloride:acetone=10:1) to obtain 176 mg (86.3%) of aimed compound. m.p. 202°–204 °C.

Example 6

Cis-3-propionylamino-4-methyl-1-(1-methylindazol-3-ylcarbonyl)pyrrolidine

Into 2 ml of DMF were dissolved 200 mg (0.68 mmol) of cis-3-amino-4-methyl-1-(1-methylindazol-3-ylcarbonyl)pyrrolidine hydrochloride and 0.09 ml (0.68 mmol) of triethylamine, and the solution was stirred for 0.5 hours at room temperature. This solution was added to another solution which was separately prepared by dissolving 0.05 ml (0.68 mmol) of propionic acid and 112 mg (0.68 mmol) of CDI into 2 ml of DMF, followed by stirring for 2 hours at room temperature. Resultant mixture was stirred overnight at room temperature. After DMF was distilled off, to the residue was added water and the solution was made alkaline with sodium bicarbonate, which was then extracted with methylene chloride. After washed with saturated saline solution and dried over anhydrous magnesium sulfate, the solution was concentrated under reduced pressure to obtain crude oil. This was subjected to silica gel column chromatographic purification (methylene chloride:acetone=5:1) to obtain 37 mg (17.3%) of aimed compound. m.p. 139°–141 °C.

Example 7

Cis-3-(N-t-butoxycarbonyl-N-methyl)amino-4-methyl-1-(1-methylindazol-3-ylcarbonyl)pyrrolidine To 74 mg (1.85 mmol) of sodium hydride (60%) was added 6 ml of DMF. To this solution was added dropwise a solution of 600 mg (1.67 mmol) of cis-3-t-butoxycarbonylamino-4-methyl-1-(1-methylindazol-3-ylcarbonyl)pyrrolidine in 6 ml of methylene chloride under cooling with ice. Then, the mixture was stirred for 1 hour at room temperature. To this solution was added 0.13 ml (2.09 mmol) of methyl iodide under water cooling, and the mixture was stirred for 1 hour at room temperature. Solvent was distilled off under reduced pressure and to the residue was added water, then the solution was extracted with methylene chloride. After washed with saturated saline solution and dried over anhydrous magnesium sulfate, the solution was concentrated under reduced pressure to obtain pale brown oil. This was subjected to silica gel column chromatographic purification (methylene chloride:methanol=30:1) to obtain aimed compound, which weighed 623 mg (quantitative) as a colorless amorphous substance.

Example 8

Cis-3-methylamino-4-methyl-1-(1-methylindazol-3-ylcarbonyl)pyrrolidine

Into 6 ml of ethanol was dissolved 520 mg (1.40 mmol) of cis-3-(N-t-butoxycarbonyl-N-methyl)amino-4-methyl-1-(1-methylindazol-3-ylcarbonyl)pyrrolidine. After addition of 3 ml of ethanol saturated with hydrogen chloride under cooling with water, the mixture was stirred overnight at the same temperature. Solvent was distilled off under reduced pressure, to the residue was added water, and the solution was made alkaline with dilute aqueous solution of sodium hydroxide, which was then extracted with methylene chloride. After washed with saturated saline solution and dried over anhydrous magnesium sulfate, the solution was concentrated under reduced pressure to obtain pale yellow oil. This was subjected to silica gel column chromatographic purification (methylene chloride:methanol=20:1 to 10:1) to obtain aimed compound, which weighed 278 mg (73.2%) as pale yellow crystals. m.p. 89°–91 °C.

Example 9

Cis-3-ethylamino-4-methyl-1-(1-methylindazol-3-ylcarbonyl)pyrrolidine (1) To 27 mg (0.68 mmol) of sodium hydride (60%) was added 1 ml of DMF. To this solution was added dropwise a solution of 220 mg (0.61 mmol) of cis-3-t-butoxycarbonyl-amino-4-methyl-1-(1-methylindazol-3-ylcarbonyl)pyrrolidine in 3 ml of DMF at room temperature. Then, the mixture was stirred for 1 hour at room temperature. To this solution was added 0.15 ml (1.88 mmol) of ethyl iodide at room temperature, and the mixture was stirred for 4 hours as it was. Solvent was distilled off under reduced pressure and to the residue was added water, then the solution was extracted with methylene chloride. After washed with saturated saline solution and dried over anhydrous magnesium sulfate, the solution was concentrated under reduced pressure to obtain pale brown oil. This was subjected to silica gel column chromatographic purification (methylene chloride:methanol=30:1) to obtain 255 mg (quantitative) of pale yellow oil, cis-3-(N-t-butoxycarbonyl-N-ethyl)amino-4-methyl-1-(1-methylindazol-3-ylcarbonyl)pyrrolidine.

(2) Into 3 ml of ethanol was dissolved 232 mg (0.60 mmol) of cis-3-(N-t-butoxycarbonyl-N-ethyl)amino-4-methyl-1-(1-methylindazol-3-ylcarbonyl)pyrrolidine obtained in (1) above metioned. After addition of 1.5 ml of ethanol saturated with hydrogen chloride under water cooling, the mixture was stirred overnight at the same temperature. Solvent was distilled off under reduced pressure, to the residue was added water, and the solution was made alkaline with dilute aqueous solution of sodium hydroxide, which was then extracted with methylene chloride. After washed with saturated saline solution and dried over anhydrous magnesium sulfate, the solution was concentrated under reduced pressure to obtain pale yellow oil. This was subjected to silica gel column chromatographic purification (methylene chloride:methanol=20:1) to obtain 119 mg (69.2%) of pale yellow crystal. m.p. 62°–64 °C.

Example 10

Cis-3-(N-ethyl-N-methyl)amino-4-methyl-1-(1-methylind-azol-3-ylcarbonyl)pyrrolidine hydrochloride Into 5 ml of methylene chloride were dissolved 240 mg (0.88 mmol) of cis-3-methylamino-4-methyl-1-(1-methylind-azol-3-ylcaronyl)pyrrolidine and 0.19 ml (1.35 mmol) of triethylamine. After addition of 0.09 ml (1.13 mmol) of ethyl iodide at room temperature, the mixture was refluxed for 3 hours. Further, 0.56 ml (7.00 mmol) of ethyl iodide were supplemented dividedly four times and the mixture was refluxed for 25 hours totally. The reaction mixture was poured into water and was made alkaline with dilute aqueous solution of sodium hydroxide, which was then extractd with methylene chloride. After washed with saturated saline solution and dried over anhydrous magnesium sulfate, the mixture was concentrated under reduced pressure to obtain pale yellow oil. This was subjected to silica gel column chromatographic purification (methylene chloride:methanol=30:1) to obtain 177 mg (66.8%) of aimed compound as a pale yellow oil.

This oil was converted to its hydrochloride according to a usual method to obtain colorless crystals of m.p. 204°-207 ° C.

Example 11

3-Dimethylamino-(1-methylindazol-3-ylcarbonyl)-pyrrolidine hydrochloride

Into 3 ml of DMF was dissolved 491 mg (2.79 mmol) of 1-methylindazol-3-carboxylic acid, and to the solution was added 452 mg (2.79 mmol) of CDI and was stirred for 2 hours at room temperature. To this solution was added at room temperature a solution obtained by dissolving 423 mg (2.79 mmol) of 3-dimethylaminopyrrolidine hydrochloride into 8 ml of DMF, adding 1.0 ml (7.1 mmol) of triethylamine and stirring for 0.5 hour at room temperature. After the mixture was stirred for 2 hours at the same temperature, DMF was distilled off under reduced pressure and to the residue was added water, then the solution was extracted with methylene chloride. After washed with saturated saline solution and dried over anhydrous magnesium sulfate, the mixture was concentrated under reduced pressure to obtain pale orange oil. This was subjected to silica gel column chromatographic purification (methylene chloride:methanol=20:1 ∘10:1) to obtain 565 mg (76.2%) of pale orange oil. This oil was dissolved with 5 ml of ethanol, was added with 0.7 ml of ethanol saturated with hydrogen chloride under cooling with ice. Deposited crystal was collected by filtration to obtain 528 mg of aimed compound. m.p. 278°-281 ° C. (decompd.)

Example 12

Cis-3-(N-ethyl-N-methyl)amino-4-methyl-1-(1-methylindol-3-ylcarbonyl)pyrrolidine hydrochloride (1) Into 6 ml of methylene chloride were dissolved 400 mg (2.28 mmol) of 1-methylindole-4-carboxylic acid and 457 mg (2.28 mmol) of cis-3-t-butoxycarbonylamino-4-methylpyrrolidine, and to the solution was added 481 mg (2.51 mmol) of 1-ethyl-3-(3'-dimethylaminopropyl)carbodiimide hydrochloride under cooling with ice. The mixture was stirred overnight at the same temperature. After completion of the reaction, the mixture was washed with water and with saturated saline solution, dried over anhydrous magnesium sulfate, and then concentrated under reduced pressure. The concentrated residue was purified with silica gel column chromatography (methylene chloride:acetone=10:1) to obtain 600 mg (73.5%) of cis-3-t-butoxycarbonylamino-4-methyl-1(1-methylindol-3-ylarbonyl)pyrrolidine.

(2) To 74 mg (1.85 mmol) of sodium hydride (60%) was added 1 ml of DMF. To this solution was added dropwise a solution of 600 mg (1.68 mmol) of cis-3-t-butoxycarbonyl-amino-4-methyl-1-(1-methylindol-3-ylcarbonyl)pyrrolidine in 3 ml of DMF at room temperature. Then, the mixture was stirred for 1 hour at room temperature. To this solution was added 0.16 ml (2.57 mmol) of methyl iodide at room temperature, and the mixture was stirred overnight as it was. Further, 0.16 ml (2.57 mmol) of methyl iodide were supplemented and the mixture was stirred for 7 hours at room temperature. Solvent was distilled off under reduced pressure and to the residue was added water, then the solution was extracted with methylene chloride. After washed with saturated saline solution and dried over anhydrous magnesium sulfate, the solution was concentrated under reduced pressure to obtain crude oil. This was subjected to silica gel column chromatographic purification (methylene chloride:acetone=20:1) to obtain 498 mg (79.8%) of colorless oil, cis-3-(N-t-butoxycarbonyl-N-methyl)amino-4-methyl-1-(1-methylindol-3-ylcarbonyl)pyrrolidine.

(3) Into 5 ml of ethanol was dissolved 498 mg (1.34 mmol) of cis-3-(N-t-butoxycarbonyl-N-methyl)amino-4-methyl-1-(1-methylindol-3-ylcarbonyl)pyrrolidine. After addition of 2.5 ml of ethanol saturated with hydrogen chloride under water cooling, the mixture was stirred for 2 hours at the same temperature. Solvent was distilled off under reduced pressure, to the residue was added water, and the solution was made alkaline with dilute aqueous solution of sodium hydroxide, which was then extracted with methylene chloride. After washed with saturated saline solution and dried over anhydrous magnesium sulfate, the solution was concentrated under reduced pressure to obtain crude oil. This was subjected to silica gel column chromatographic purification (methylene chloride:methanol=10:1) to obtain 243 mg (66.8%) of pale yellow oil, cis-3-methylamino-4-methyl-1-( 1methylindol-3-ylcarbonyl ) pyrrolidine.

(4) Into 10 ml of methylene chloride were dissolved 240 mg( 0.88 mmol) of cis-3-methylamino-4-methyl-1-( 1-methylindol-3-ylcarbonyl)pyrrolidine and 0.18 ml ( 1.30 mmol) of triethylamine. After addition of 0.2 ml (2.50 mmol) of ethyl iodide at room temperature, the mixture was refluxed for 35 hours. The reaction mixture was poured into water and made alkaline with dilute aqueous solution of sodium hydroxide, which was then extracted with methylene chloride. After washed with saturated saline solution and dried over anhydrous magnesium sulfate, the solution was concentrated under reduced pressure to obtain pale yellow oil. This was subjected to silica gel column chromatographic purification (methylene chloride:methanol=20:1) to obtain 101 mg (38.1%) of aimed compound as a pale yellow oil. This oil was converted to its hydrochloride according to an usual method to obtain colorless crystals with m.p. 94°-97 ° C.

Example 13

Cis-3-(N-methyl-N-n-propyl)amino-4-methyl-1-(1-methylindazol-3-ylcarbonyl)pyrrolidine hydrochloride To 9 ml of DMF were added 440 mg (1.62 mmol) of cis-3-methylamino-4-methyl-1-(1-methylindazole-3-ylcarbonyl)pyrrolidine and 670 mg (4.85 mmol) of anhydrous potassium carbonate. After 670 mg (4.85 mmol) of n-propyl methanesulfonate was added thereto while stirring at room temperature, the mixture was stirred for 17 hours at 60 ° C. Solvent was distilled off under reduced pressure and to the residue was added water, the solution was extracted with methylene chloride. After washed with saturated saline solution and dried over anhydrous magnesium sulfate, the solution was concentrated under reduced pressure to obtain pale yellow oil. This was subjected to silica gel column chromatographic purification (methylene chloride:methanol=20:1) to obtain 355 mg (69.8%) of aimed compound. This oil, 115 mg, was dissolved with 1 ml of ethanol, added with 0.01 ml of ethanol saturated with hydrogen chloride under ice cooling and concentrated, which was then crystallized from ether to obtain 86 mg of aimed compound. m.p. 127°–130 ° C. (decompd.)

Pharmacological experiment 1: 5-HT$_3$-binding assay

The specific 5-HT$_3$ receptor-binding assay was performed according to the method by G. J. Kilpatrick et al. using [$^3$H] GR 65630 as a tracer ligand.

A crude specimen of synaptic membrane was prepared from the cerebral cortex of rat and used for experiment by suspending it into 50 mM HEPES buffer (pI 7.4) added with Triton X- 100.

Next, testing compounds of several kinds of concentration and tritium-labelled GR 65630 (final concentration 0.2–0.3 nM) were added to the suspension of membrane and allowed to react for 30 minutes at 23 ° C. After the reaction, the reaction mixture was filtered under suction and the filter was washed with 50 mM HEPES buffer. Then, the radioactivity left behind on the filter was determined with a liquid scintillation counter.

The nonspecific binding was determined in the presence of 100 μM metoclopramide.

Then, 50% inhibitory concentration (IC50) of the compounds of Examples 10 through 12 was determined graphically (Table 1).

TABLE 1

| Test compound (Example No.) | 5-HT$_3$-binding assay IC$_{50}$ (nM) |
| --- | --- |
| 10 | 1 |
| 11 | 3 |
| 12 | 2 |

Pharmacological experiment 2: Antagonistic action on von Bezold Jarisch reflex

The antagonistic action of testing compounds to 5-HT$_3$ was assayed according to the method described in Naunyn-Schmiedeberg's Arch. Pharmacol., vol. 326, 36 (1984).

Under the anesthetization of rat with urethane/chloralose, the blood pressure was monitored with hemodynamometer frown carotid arteries and the heart rate was monitored from electrocardiogram. The compounds of Examples 10, 11 and 12 among the compounds of the present invention inhibited the reflex bradycardia caused through the intravenous administration of 1 mg/kg of 5-HT.

Utilizability in the industry

The compounds of the general formula I in the present invention have excellent antagonistic action to 5-HT$_3$ receptor and are useful as medicinal drugs.

We claim:

1. N,N'-disubstituted amide drivatives represented by a general formula

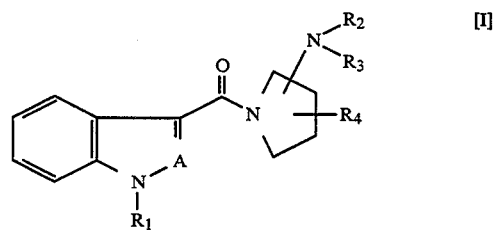

(wherein R$_1$ denotes a hydrogen atom or lower alkyl group, R$_2$ and R$_3$, which may be identical or different, denote respectively a hydrogen atom, lower alkyl group, lower alkenyl group, nonsubstituted or substituted aryl-lower alkyl group, acyl group or lower alkoxycarbonyl group, R$_4$ denotes a hydrogen atom, lower alkyl group or lower alkoxy group, and A denotes CH or N), their hydrates or acid addition salts.

2. The compound of claim 1 which is cis-3-(N-ethyl-N-methyl)amino-4-methyl-1-(1-methylindazol-3ylcarbonyl)pyrrolidine hydrochloride.

3. The compound of claim 1 which is 3-dimethylamino-(1-methylindazol-3-ylcarbonyl)pyrrolidine hydrochloride.

4. The compound of claim 1 which is cis-3-(N-ethyl-N-methyl)amino-4-methyl-1-(1-methylindol-3ylcarbonyl)pyrrolidine hydrochloride.

5. The compound of claim 1 wherein R$_4$ is a lower alkyl group.

6. The compound of claim 1 wherein R$_4$ is a lower alkoxy group.

* * * * *